United States Patent
Feenstra et al.

(10) Patent No.: US 6,214,829 B1
(45) Date of Patent: Apr. 10, 2001

(54) PIPERAZINE COMPOUNDS, THEIR PREPARATION, AND METHODS OF USING THEM

(75) Inventors: Roelof W. Feenstra; Gerben M. Visser; Cornelis G. Kruse; Martinus T. M. Tulp; Stephen K. Long, all of Weesp (NL)

(73) Assignee: Duphar International Research B.V. (NL)

( * ) Notice: Subject to any disclaimer, the term of this patent is extended or adjusted under 35 U.S.C. 154(b) by 0 days.

(21) Appl. No.: 09/144,076

(22) Filed: Aug. 31, 1998

(30) Foreign Application Priority Data

Sep. 2, 1997 (EP) .................................................. 97202704

(51) Int. Cl.[7] ...................... A61K 31/496; C07D 401/04
(52) U.S. Cl. ...................... 514/253.06; 544/363
(58) Field of Search ............................ 544/363; 514/254, 514/253.06

(56) References Cited

U.S. PATENT DOCUMENTS

| | | | |
|---|---|---|---|
| 4,737,505 | 4/1988 | Guillaume et al. | 514/323 |
| 5,486,518 | 1/1996 | Yardley et al. | 514/254 |
| 5,519,025 | 5/1996 | Yardley et al. | 514/254 |
| 5,627,177 | * 5/1997 | Cliffe et al. | 514/212 |

FOREIGN PATENT DOCUMENTS

| | | |
|---|---|---|
| 138 280 | 4/1985 | (EP) . |
| 169 148 | 1/1986 | (EP) . |
| 372 657 | 6/1990 | (EP) . |
| 512 755 | 11/1992 | (EP) . |
| 650 964 | 5/1995 | (EP) . |
| 785 195 | 7/1997 | (EP) . |
| WO 94/13659 | 6/1994 | (WO) . |
| WO 94/15919 | 7/1994 | (WO) . |

\* cited by examiner

*Primary Examiner*—Richard L. Raymond
(74) *Attorney, Agent, or Firm*—Finnegan, Henderson, Farabow, Garrett & Dunner, L.L.P.

(57) ABSTRACT

Novel piperazine and piperidine derivative compounds having interesting and advantageous pharmacological properties. The disclosed compounds have the general formula (a)

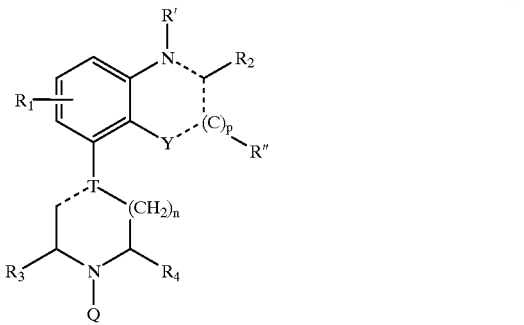

and salts thereof. These compounds have high affinity for both the dopamine $D_2$ receptors and serotonine $5\text{-}HT_{1A}$ receptors, rendering them useful for the treatment of CNS-disorders, in particular schizophrenia.

8 Claims, No Drawings

PIPERAZINE COMPOUNDS, THEIR PREPARATION, AND METHODS OF USING THEM

The present invention relates to a group of new piperazine compounds having interesting and advantageous pharmacological properties.

The inventors have discovered that compounds of the formula (a)

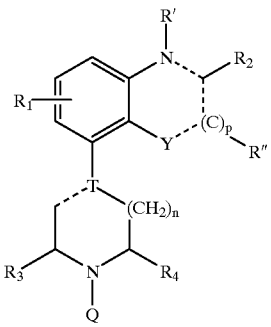

wherein
- $R_1$ is hydrogen or fluoro,
- R' is H or $C_{1-4}$-alkyl,
- $R_2$ is H, $C_{1-4}$-alkyl or an oxo group, or R' and $R_2$ together represent a single bond,
- R" is H or $C_{1-4}$-alkyl, and the dotted lines represent a single or double bond,
- p has the value 0, 1, or 2,
- Y represents C, O, N or S,
- T represents N or C,
- $R_3$ and $R_4$ independently are hydrogen or $C_{1-4}$-alkyl,
- n has the value 1 or 2,
- Q is a group of the formula —$CH_2$—$C(R_5R_6)$—Z—$R_7$, wherein $R_5$ and $R_6$ represent H or $C_{1-7}$-alkyl, $C_{1-3}$-alkylphenyl; Z represents —$C(R_8R_9)$—O—, —$C(R_8R_9)$—$C(=O)$—, —$C(R_8R_9)$—$C(=NOR_{10})$—, —NH—$C(=O)$— or —O—$CH_2$—, wherein $R_8$, $R_9$, and $R_{10}$ represent H or $C_{1-4}$-alkyl; and $R_7$ is a 5- or 6-membered cyclic group, aromatic group or hetero-aromatic group, or the 1- or 2-adamantyl group, which $R_7$ group can be substituted with O—$C_{1-4}$-alkyl, CN, halogen or C-$_{1-4}$-alkyl, with the proviso that $R_7$ cannot be 1-alkylcycloalkyl, and the proviso that the compounds of formula (a) wherein Z is the group —NH—$C(=O)$—, $R_5$=$R_6$=H, T is nitrogen, and the bicyclic group is 1,4-benzoxazin-8-yl, quinoxalin-5-yl, quinolin-5-yl, indol4-yl, benzoxazol-7-yl, benzimidazol-4-yl, or benzothiazol-7-yl are not included, and salts thereof have interesting and advantageous pharmacological properties.

Preferred compounds according to the invention are compounds having formula (a) wherein T represents nitrogen, R' is hydrogen, and the other symbols have the above meanings.

Especially preferred are compounds of formula (a) wherein Y is carbon and T is nitrogen, p=1, n=1, $R_1$, R', $R_2$, R", $R_3$ and $R_4$ are hydrogen, the dotted lines are single bonds, and Q is a group of the formula —$CH_2$—$C(R_5R_6)$—Z—$R_7$ wherein $R_5$ and $R_6$ represent H, $C_{1-4}$-alkyl or benzyl, Z is —$C(R_8R_9)$—$C(=O)$—, —$C(R_8R_9)$—O— or —NH—$C(=O)$—, wherein $R_8$ and $R_9$ represent hydrogen or methyl, and $R_7$ is phenyl optionally substituted with halogen, CN, $CH_3$ or $OCH_3$. In these especially preferred compounds, if Z is —NH—$C(=O)$— or —$CH_2$—O—, $R_5$=H and $R_6$ is alkyl or alkylphenyl, then the R-configuration at the chiral C-atom carrying $R_5$ and $R_6$ is preferred.

It is known from EP 0650964 that compounds of the formula

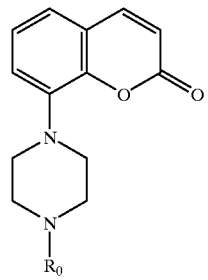

wherein $R_0$ is $C_{1-4}$-alkyl, which compounds can be substituted in the phenyl group and/or heterocyclic group and/or the piperazine group, act on the central nervous system by binding to 5-HT receptors. In particular, these compounds bind to subtypes of the 5-HT-receptor, i.e. 5-$HT_{1A}$ and 5-$HT_{1D}$ receptors.

It has now surprisingly been found that the compounds according to the invention show high affinity for both the dopamine $D_2$ and serotonin 5$HT_{1A}$ receptors (pKi range 7.0–9.5 for both receptor types). Affinity for this combination of receptors is useful for the treatment of schizophrenia and other psychotic disorders and allows for a more complete treatment of all disease symptoms, e.g., positive symptoms, negative symptoms and cognitive deficits.

The compounds according to the invention show varying activities as either partial agonists or antagonists at dopamine $D_2$-, $D_3$-, and $D_4$-receptors. Some of the inventive compounds show agonist-like effects at dopamine receptors, however they potently antagonize apomorphine-induced climbing behavior in mice ($ED_{50}$ values<1 mg/kg p.o). The inventive compounds also show varying activity as 5-$HT_{1A}$ receptor agonists and induce aspects of the serotonin behavioral syndrome to differing intensities.

The inventive compounds are active in therapeutic models sensitive to clinically relevant antipsychotics (e.g., the conditioned avoidance response; Van der Heyden & Bradford, Behav. Brain Res., 1988, 31:61–67, the disclosure of which is incorporated herein by reference), antidepressants (e.g., differential reinforcement of low rate responses; van Hest et al., Psychopharmacology, 1992, 107:474–479, the disclosure of which is incorporated herein by reference), and anxiolytics (e.g., suppression of stress-induced vocalization; van der Poel et al., Psychopharmacology, 1989,97:147–148, the disclosure of which is incorporated herein by reference).

In contrast to clinically relevant dopamine $D_2$ receptor antagonists, the presently described compounds have a low propensity to induce catalepsy in rodents and as such are likely to induce less extrapyramidal side effects than existing antipsychotic agents.

The 5-$HT_{1A}$ receptor agonism inherent in these compounds may be responsible for the reduced tendency to induce extrapyramidal effects and the therapeutic effects observed in behavioral models sensitive to either antidepressants or anxiolytics.

The inventive compounds are additionally expected to be of value for the treatment of affective disorders or diseases of the central nervous system caused by disturbances in either the dopaminergic or serotinergic systems, for example, aggression, anxiety disorders, autism, vertigo, depression, disturbances of cognition or memory, and in particular schizophrenia, and other psychotic disorders.

Suitable acids with which the compounds can form pharmaceutically acceptable acid addition salts include hydrochloric acid, sulphuric acid, phosphoric acid, nitric acid, and organic acids such as citric acid, fumaric acid, maleic acid, tartaric acid, acetic acid, succinic acid, benzoic acid, p-toluene sulphonic acid, methanesulphonic acid and naphthalene-sulphonic acid.

The compounds of the invention can be brought into forms appropriate for administration by means of the usual processes known to the skilled artisan using auxiliary substances such as liquid and solid carrier materials.

The compounds of the invention can be obtained according to a number of synthetic routes (A to D) as described hereafter. The piperazines and homopiperazines used in these methods are indicated as I-H to XVIII-H, wherein I to XVIII represent the following groups (FIG. 1):

FIG. 1

I

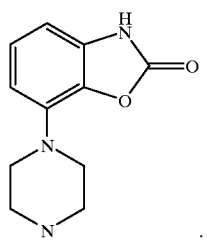

II

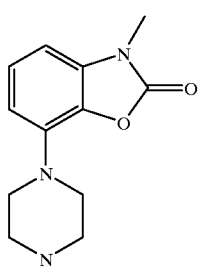

III

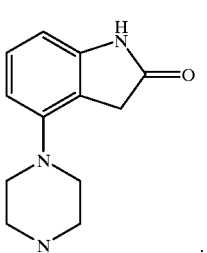

IV

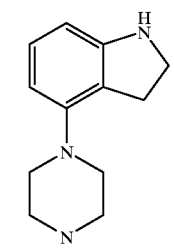

-continued

V

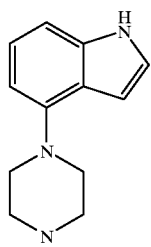

VI

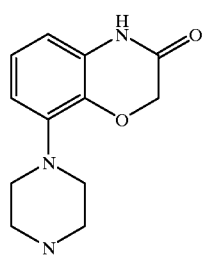

VII

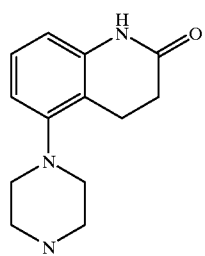

VIII

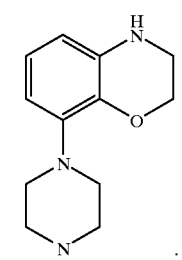

IX

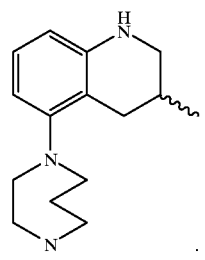

X 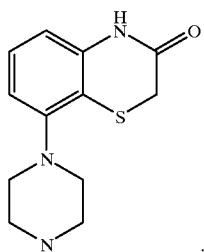
XI 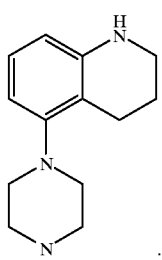
XII 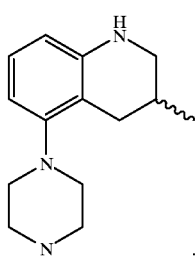
XIII 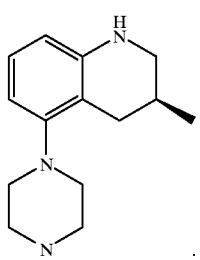
XIV 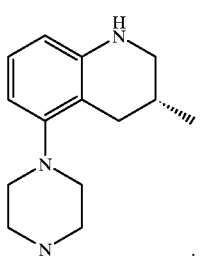
XV 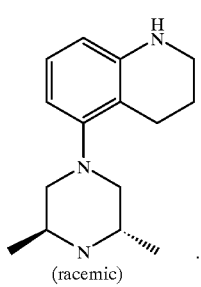
(racemic)
XVI 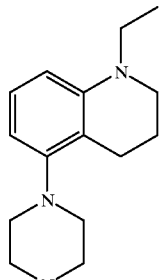
XVII 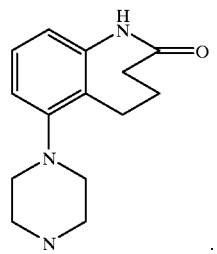
XVIII 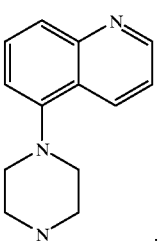
The syntheses of the piperazines I-H, IV-H, V-H, VI-H, VIII-H, XI-H, XII-H and XVIII-H have been described in EP 0189612 and/or EP 0138280, the disclosures of both of which are incorporated herein by reference, or can be prepared in an analogous manner. The syntheses of the remaining piperazines is given below (schemes i to vii).
scheme i
Synthesis of II-H:
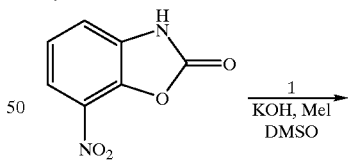
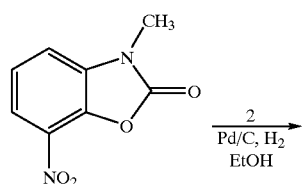
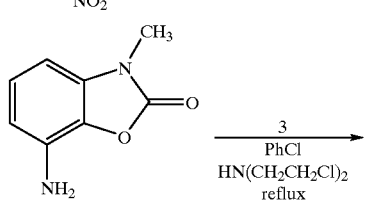

-continued

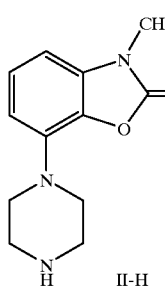

II-H

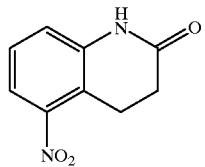

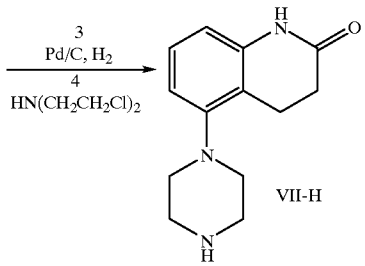

VII-H

Step 1 (scheme iii)

This step can be carried out according to the procedure described in: C. K. Ingold, H. A. Piggott, *J. Chem. Soc.(II)*, (1923),1469, the disclosure of which is incorporated herein by reference.

Step 2 (scheme iii)

This step can be carried out according to the procedure described in: M. Tomita, S. Minami, *J. Chem. Soc. (C)*, (1969), 183, the disclosure of which is incorporated herein by reference.

Steps 3 and 4 (scheme iii)

Steps 3 and 4 can be carried out according to procedures described in EP 0189612.

scheme ii

Synthesis of III-H:

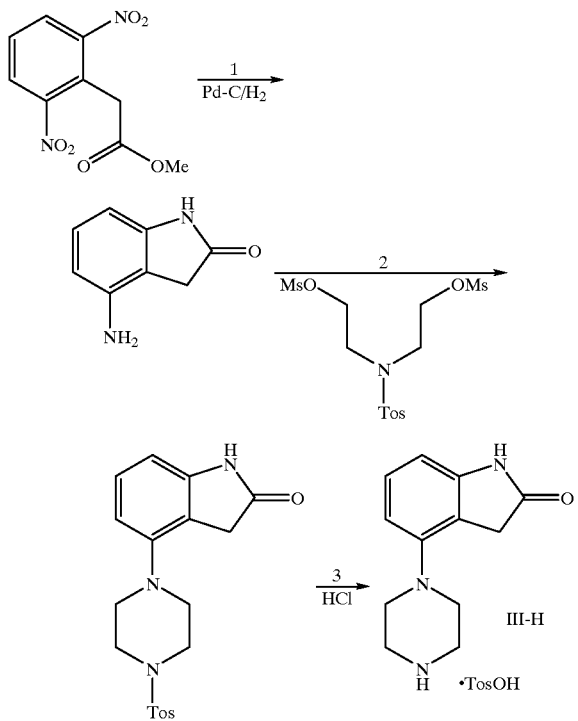

III-H · TosOH scheme iv

Synthesis of IX-H:

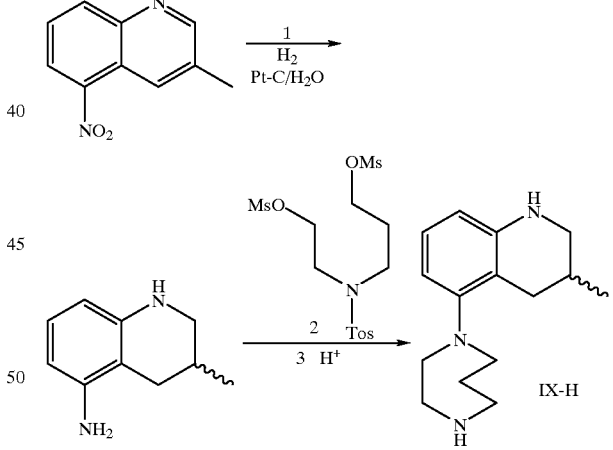

IX-H scheme iii

Synthesis of VII-H:

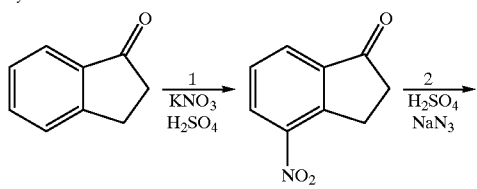

Moiety of X-H

X-H was not used as an intermediate in the synthesis. The fragment was built in a different manner, see "Remark about D3" in the last part of the examples (vide infra).

Synthesis of XII-H scheme v

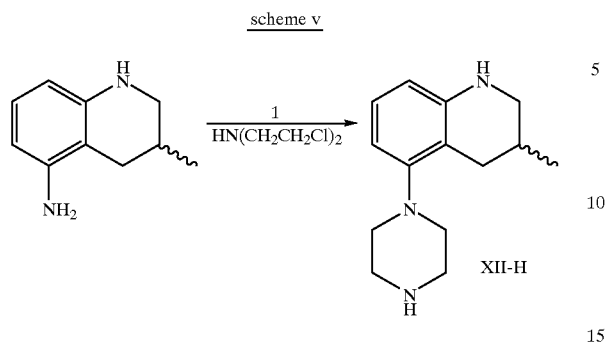

Step 1 (scheme v)

Transforming the aniline (see also scheme iv) into the corresponding piperazine XII-H can be carried out according to the procedure described in EP 0189612.

scheme vi

Synthesis of XV-H:

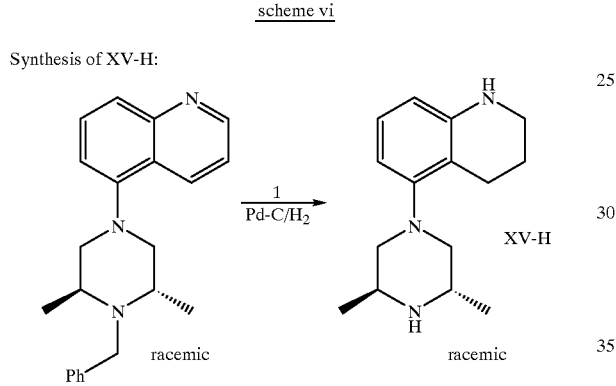

scheme vii

Synthesis of XVII-H:

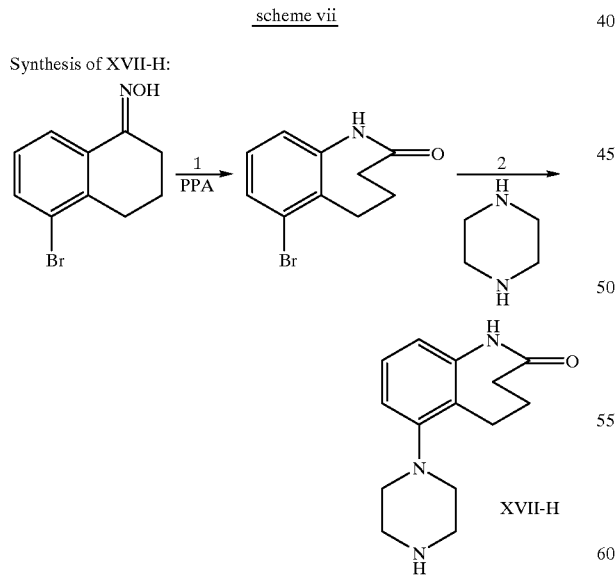

The H-atom of the N-H moiety of compounds I-H to XVII-H can be replaced by group Q in four different chemical ways (A, B. C, and D, vide infra), ultimately leading to the compounds of the invention.

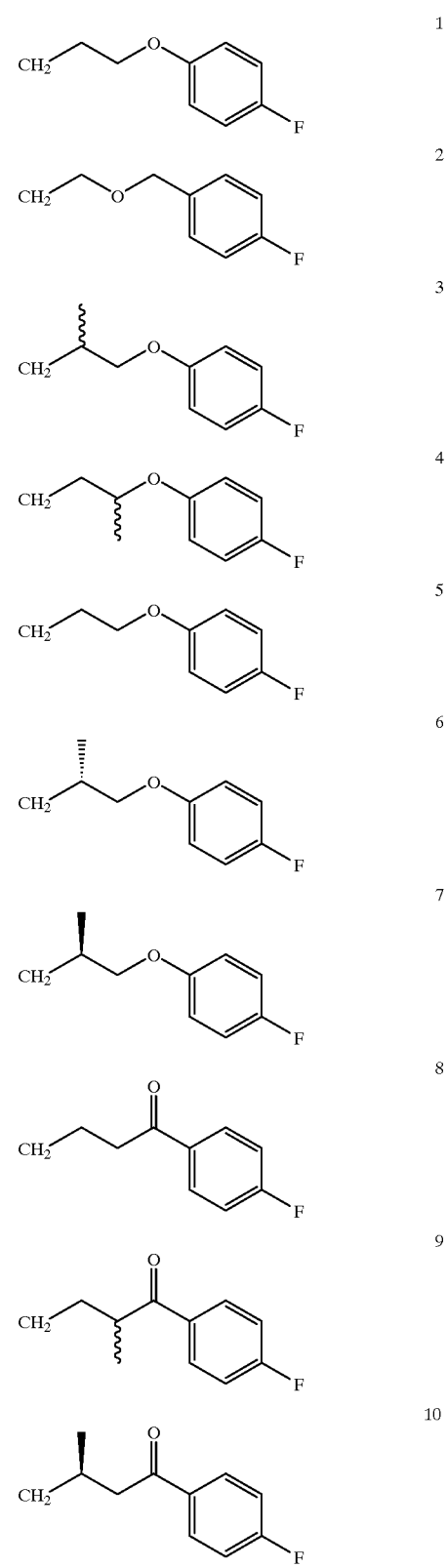

-continued
11
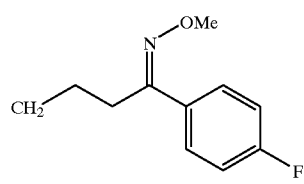
12
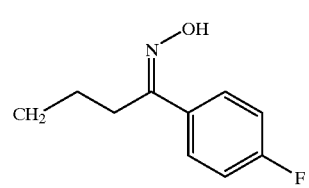
13
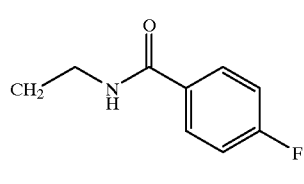
14
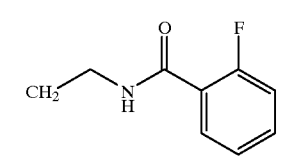
15
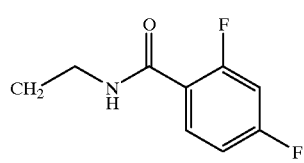
16
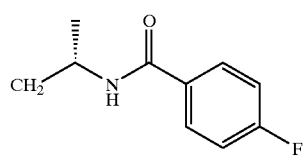
17
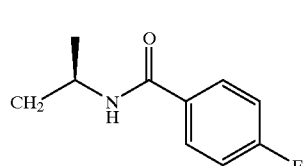
18
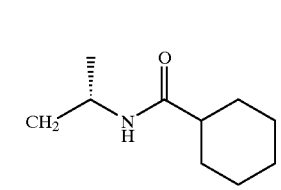
18
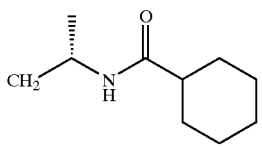
19
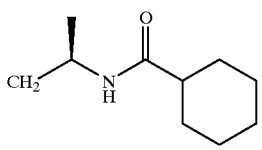
20
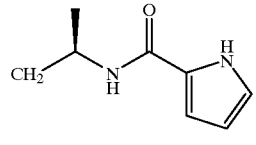
21
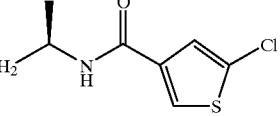
22
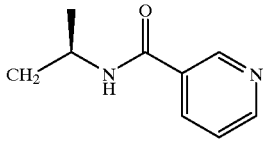
23
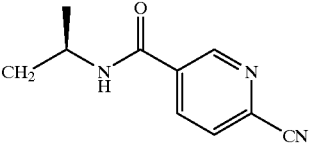
24
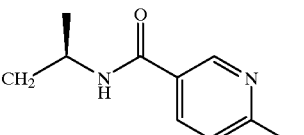
25
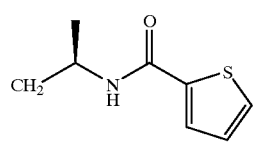
26
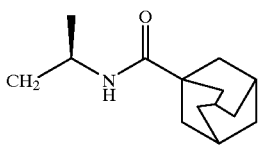

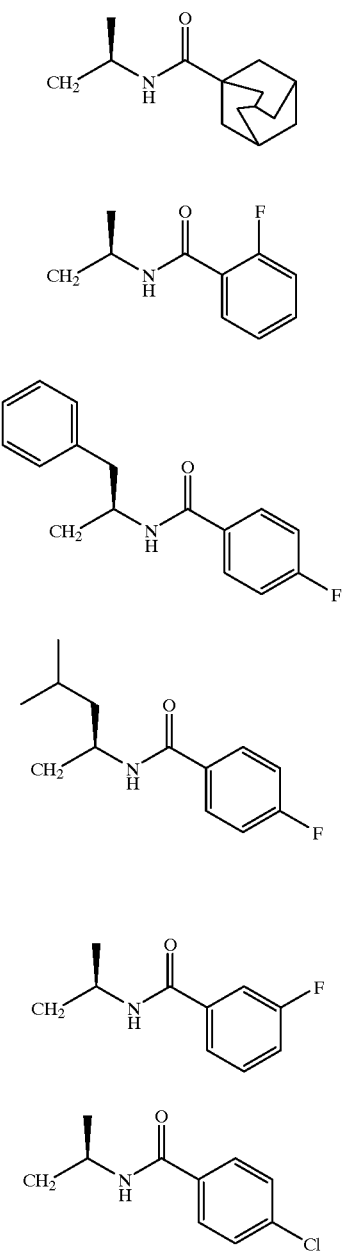

Fig. 2

A number of Q-Cl or Q-Br compounds are commercially available, others can be obtained according to standard chemical procedures as illustrated in the examples showing the preparation of these intermediates.

Synthesis routes A to D

The compounds listed in Table A, except for A11, A14 and A16, were prepared via the synthesis depicted in scheme A1 (vide infra): a piperazine (see FIG. 1) was reacted with Q-X (X=Cl, Br, OMs, OTos) in e.g., acetonitrile with Et(i-Pr)$_2$N acting as a base; in some cases KI (or NaI) was added. Et$_3$N can be used instead of Et(i-Pr)$_2$N.

Compounds A11, A14 and A16 were prepared according to the synthesis given in scheme A2: reaction of A2 and A8 with hydroxylamine (derivatives) yielded the desired compounds.

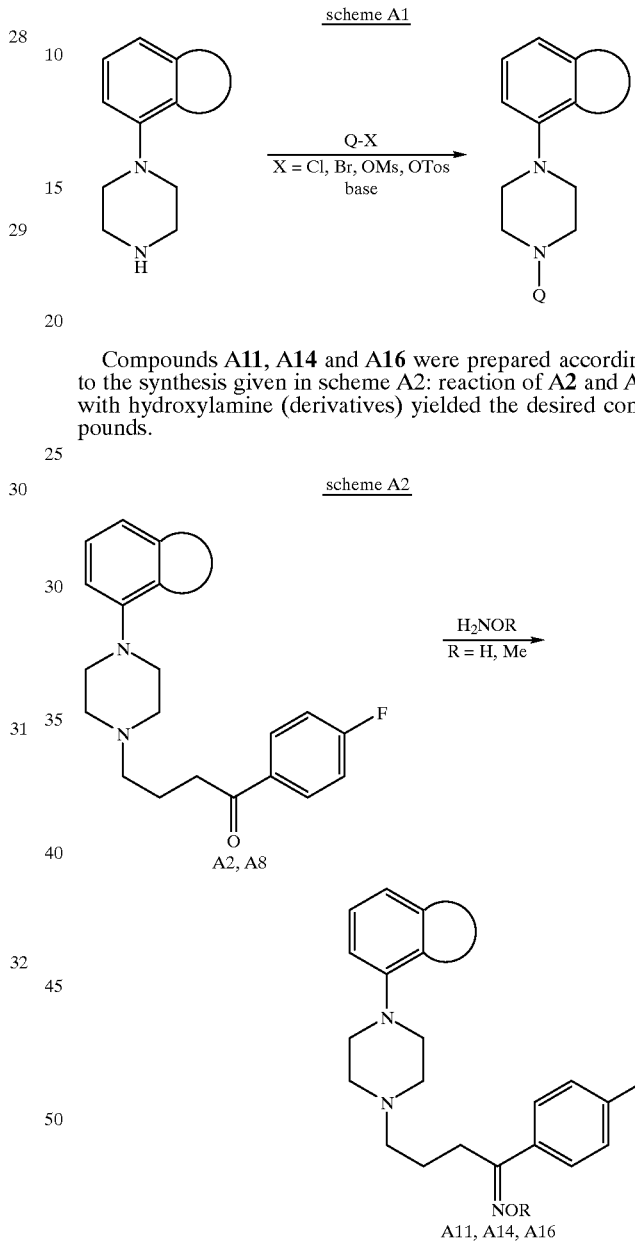

Compound A23 can be obtained according to a variation of the synthesis depicted in scheme A1, as indicated below in scheme A3.

scheme A3

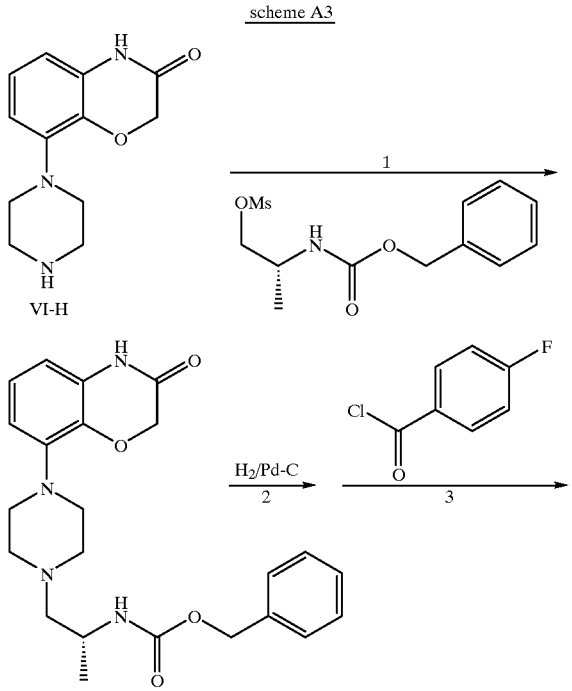

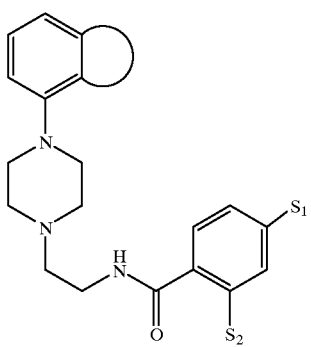

In scheme C, a piperazine is coupled to a protected amino acid (step 1) to yield an intermediate which gives after two reductions (steps 2,3) a (optically active) primary amine. This amine can be derivatzed easily by treatment with e.g., acid chlorides (step 4), yielding the products of the invention.

scheme C

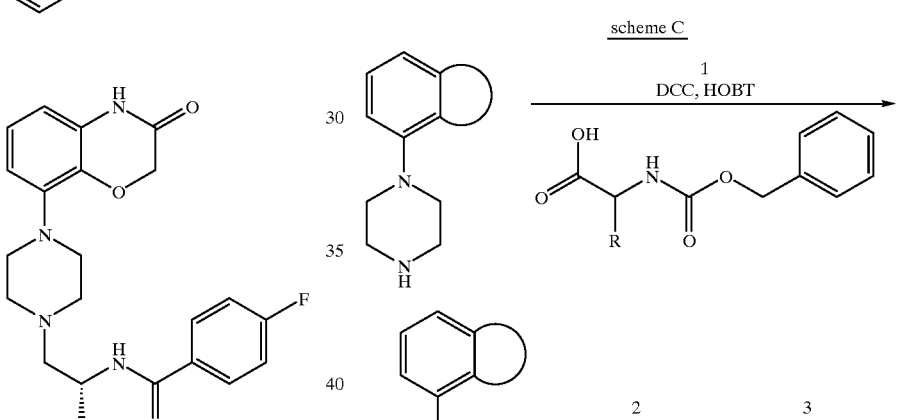

The compounds listed in table B infra, were synthesized according to the reaction depicted in scheme B. Piperazines were reacted with N-benzoyl-aziridines to yield the compounds of the invention.

scheme B

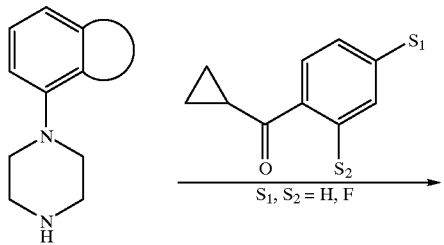

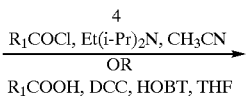

$S_1, S_2 = H, F$

17
-continued

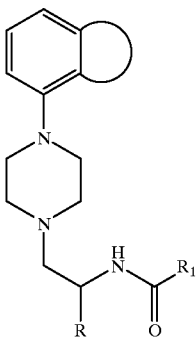

According to route D, the synthesis of the desired compounds is achieved by reacting a piperazine with the optically active (R)-2-para-fluorophenyl-4-methyl-4,5-dihydro-oxazole, scheme D

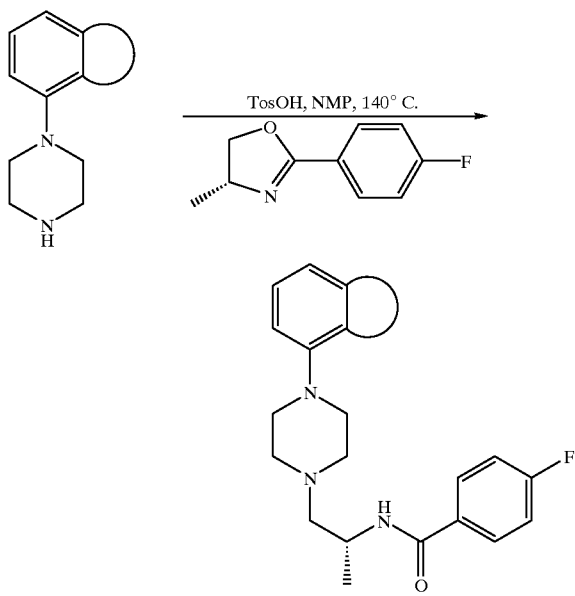

The preparation of the compounds of formula (a) and of a number of intermediate compounds will now be described in detail in the following Examples, which are intended to be purely exemplary and not limiting of the disclosed invention.

Abbreviations:

| | |
|---|---|
| BINAP | bis(diphenylphosphino)-1,1'-binaphthyl |
| dba | dibenzylideneacetone.(1,5-diphenyl-1,4-pentadien-3-one) |
| DCC | dicyclohexylcarbodiimide |
| DMSO | dimethylsulfoxide |
| $Et_3N$ | triethylamine |
| $Et(i-Pr)_2N$ | diisopropylethylamine |
| EtOAc | ethyl acetate |
| HOBT | 1-hydroxybenztriazole |
| Ms | mesyl |
| Tos | tosyl |

18
EXAMPLES

Example 1

Preparation of A8.2HCl (See Scheme A1)

While stirring, 0.7 g (3.2 mmol) of piperazine XI-H was dissolved in 20 ml of acetonitrile, after which 0.5 g (3.9 mmol) of di-isopropyl-ethyl-amine and 0.65 g (3.2 mmol) of Q8-Cl were added. The reaction midure was refluxed for 18 hrs, after which the reaction was allowed to reach room temperature. The reaction mixture was concentrated in vacuo, after which the residue was subjected to column chromatography (SiO$_2$, eluent: CH$_2$Cl$_2$/MeOH=98/2), yielding 0.4 g of an oil. The latter oil was treated with 2.5 equivalents of 0.5 M HCl/MeOH, yielding 0.4 g of almost pure A8.2HCl. m.p.: dec.>260° C. $^1$H-NMR(CDCl$_3$/DMSO=¼ δ: 1.95(m, 2H), 2.13(m, 2H), 2.77(m, 2H), 3.10–3.30(cluster, 10H), 3.33(m, 2H), 3.40–3.90(cluster, 2H), 6.86–7.04(cluster, 2H), 7.24(t, 1H), 7.34(m, 2H), 8.08 (m, 2H), 10.8(broad, 1H).

Example 2

Preparation of A11.2HCl (See Scheme A2)

0.54 g (1.4 mmol) of A8 (free base) was dissolved in 15 ml of MeOH together with 0.11 ml of pyridin and 0.14 g (1.67 mmol) of MeONH$_2$.HCl. The reaction mixture was stirred and heated at 50° C. for 2.5 hrs. After this period, an extra equivalent of MeONH$_2$.HCl and 1 ml of di-isopropyl-ethyl-amine were added, and the reaction was continued for 6 hrs. The reaction mixture was allowed to reach room temperature, after which it was concentrated in vacuo. The residue was taken in saturated NaHCO$_3$ solution, and the latter was extracted with EtOAc. The organic fraction was dried or MgSO$_4$, after removal of the drying agent and the solvent in vacuo, the resulting oil was subjected to column chromatography (SiO$_2$, eluent: EtOAc), yielding 0.40 g of a brownish oil which subsequently was treated with 2.5 equivalents of 0.5 M HCl/MeOH to yield 0.37 g (0.77 mmol, 55%) of A11.2HCl as a white solid. m.p.: 218–222° C. $^1$H-NMR(CDCl$_3$/DMSO=¼)δ: 1.92–2.04(m, 4H), 2.72–2.84(m, 4H), 3.10–3.28(cluster, 8H), 3.34(m, 2H), 3.53(m, 2H), 3.95(s, 3H), 6.98(m, 2H), 7.20(m, 2H), 7.25(t, 1H), 7.76(m, 2H), 11.05(broad, 1 H), 10.2–11.8(broad, 1 H). The E/Z ratio was 95/5.

Example 3

Preparation of A3 (See Scheme A3)

Step 1 (scheme A3): 1.62 g (7 mmol) of piperazine VI-H, 2.0 g (7 mmol) of O-mesyl-N-benzyloxycarbonyl-(R)-alaninol, 0.84 g (8.4 mmol) of Et$_3$N and a small amount of KI were dissolved in 30 ml of acetonitrile. While stirring, the reaction mixture was refluxed for 0.5 hr during which a white precipitate formed. The precipitate was removed by filtration. To the filtrate, SiO$_2$ was added and the resulting slurry was subjected to evaporation to remove the acetonitrile. The resulting dry SiO$_2$ powder with the reaction mixture absorbed on it, was placed on top of a dr SiO$_2$ column (flexible), after which elution was performed with EtOAc. The product containing part of the column was cut out and the product was washed from the SiO$_2$ with MeOH. The resulting MeOH solution was concentrated and subsequently EtOAc was added, the latter solution being dried on MgSO$_4$. After removal of the drying agent and the solvent in vacuo, the pure intermediate product was isolated in 25% yield (0.75 g).

Step 2 (scheme A3): 0.75 g (1.8 mmol) of the latter compound (pure intermediated product) was dissolved in a mixture of 4 ml of EtOAc and 8 ml of MeOH. Then, under a nitrogen atmosphere, a little of 10% Pd-C was added to the mixture after whichL hydrogenation was performed. After 2 hrs, the reaction mixture was filtered and the filtrate concentrated in vacuo leaving a residue of 0.48 g (93%) of crude primary amine. This was used without further purification in step 3.

Step 3 (scheme A3): 0.48 g (1.65 mmol) of primary amine was dissolved in 20 ml of $CHCl_3$. While stirring, 0.33 g (3.3 mmol) of $Et_3N$ and 0.26 g (1.65 mmol) of para-fluorobenzoylchloride were added. After 16 hrs, $SiO_2$ was added to the reaction mixture and the resulting slurry was subjected to evaporation to remove the $CHCl_3$. The resulting dry $SiO_2$ powder with the reaction mixture absorbed on it, was placed on top of a dry $SiO_2$ column (flexible), after which elution was performed with EtOAc. The product containing part of the column was cut out and the product was washed from the $SiO_2$ with MeOH. The resulting MeOH solution was concentrated and subsequently EtOAc was added, the latter solution being dried on $MgSO_4$. After removal of the drying agent and the solvent in vacuo, 0.25 g (36%) of the free base of A23 was obtained. m.p.: 245–7° C. $^1$H-NMR($CDCl_3$/DMSO=¼) δ: 1.18(d, 3H, J=6 Hz), 2.35(dd, 1H, J=7 and J=12 Hz), 2.54–2.62(m, 5H), 2.98(m, 4H), 4.23(m, 1H), 4.5(s, 2H), 6.50–6.56(cluster, 2H), 6.82(t, 1H, J≈8 Hz), 7.23(m, 2H), 7.92(m, 2H), 8.12(d, 1H, J=8 Hz), 10.5(s, 1H).

Remark

A20 was prepared from piperazine I-X and the crude diethylketal of Q10-Br (for the preparation of the latter, see preparation of Q10-Br) according to scheme A1. This yields the diethylketal of the product A20, which was transformed into A20.HCl by treating the diethyl ketal with aqueous 2 M HCl.

TABLE A

| compound | piperazine | Q | X | salt | melting point ° C. |
|---|---|---|---|---|---|
| A1 | I | 1 | Cl | HCl | 225–7 |
| A2 | I | 8 | Cl | HCl | 260–3 |
| A3 | I | 5 | OMs | HCl | 180–2 |
| A4 | XII | 1 | Cl | 2HCl | 201–4 |
| A5 | XI | 1 | Cl | 2HCl | 218–20 |
| A6 | I | 3 | Cl | HCl | 209–12 |
| A7 | I | 4 | OTos | HCl | 205–8 |
| A8 | XI | 8 | Cl | 2HCl | >260 d |
| A9 | XI | 3 | Cl | 2HCl | 190–2 |
| A10 | XI | 4 | OTos | 2HCl | 225–9 |
| A11 | XI | 11 | prep. from A8 | 2HCl | 218–21 |
| A12 | I | 2 | OMs | — | 154–5 |
| A13 | XI | 2 | OMs | 1.3HCl | 186–7 |
| A14 | I | 11 | prep. from A2 | HCl | 224–7 |
| A15 | I | 9 | Br | HCl | 150–5 |
| A16 | XI | 12 | prep. from A8 | — | 171–3 |
| A17 | II | 1 | Cl | — | 137–8 |
| A18 | I | 7 | OMs | HCl | 207.5–10 |
| A19 | XI | 9 | Br | 2HCl | >140 d |
| A20 | I | 10 | Br | HCl | >130 d |
| A21 | XI | 7 | OMs | FUM | foam |
| A22 | I | 6 | OMs | HCl | 204–6 |
| A23 | VI | 17 | OMs | — | 245–7 |
| A24 | IX | 1 | Cl | 2HCl | 20 |

"d"/"dec" = decomposition
"foam" and "amorf" indicate a non-crystalline product was obtained.

Example 4

Preparation of B4 (See Scheme B)

A solution of 0.75 g (3.45 mmol) of piperazine XI-H in 10 ml of dry tetrahydrofuran (THF) was added to a solution of 0.63 g (3.79 mmol) of N-(para-fluoro-benzoyl)aziridine in 8 ml of dry THF. The reaction mixture was stirred at reflux temperature for 2 hrs after which it was allowed to reach room temperature. The solvent was removed in vacuo, and the residue subjected to flash column chromatography ($SiO_2$, eluent: $CH_2Cl_2$/MeOH=98/2), yielding 0.51 g (39%) of glassy product B4. m.p.: 150–2° C. $^1$H-NMR($CDCl_3$/DMSO ¼) δ: 1.88 (m, 2H), 2.55–2.65(cluster, 8H), 2.94(m, 4H), 3.30(m, 2H), 3.57(m, 2H), 3.87(broad, 1H), 6.26(d, 1H, J=8Hz), 6.38(d, 1H, J=8 Hz), 6.87(t broad, 1H), 6.95(t, 1H, J=8 Hz), 7.13(m, 2H), 7.81 (m, 2H).

TABLE B

| compound | piperazine | Q | salt | melting point ° C. |
|---|---|---|---|---|
| B1 | XII | 13 | 2HCl | 192–5 |
| B2 | XV | 13 | 2HCl | 230–3 |
| B3 | I | 13 | — | >300 dec |
| B4 | XI | 13 | — | 150–2 |
| B5 | I | 14 | — | 235–8 |
| B6 | I | 15 | — | 265–70 |
| B7 | XIII | 13 | — | 178–9 |
| B8 | XIV | 13 | — | 179–80 |

Example 5

Preparation of C10.2HCl (See Scheme C)

Step 1 (scheme C): 3.2 g (15 mmol) of piperazine VIII-H was dissolved in 45 ml of dry THF. While stirring and under a nitrogen atmosphere, 3.35 g (15 mmol) of (R)-N-(benzyloxycarbonyl)-alanine and 2.03 g (15 mmol) of 1-hydroxybenztriazol were added to the solution. The resulting mixture was brought to 0° C., after which 3.0 g (15 mmol) of dicyclohexylcarbodiimide were added. After 1.5 hrs the precipitate was removed by filtration. To the filtrate $SiO_2$ was added after which the solvent was removed. The resulting dry $SiO_2$ powder with the reaction mixture absorbed on it, was placed on top of a dr $SiO_2$ column (flexible), after which elution was performed with EtOAc/MeOH/$NH_4$OH=97/2.7/0.3. The product-containing part of the column was cut out and the product was washed from the $SiO_2$ with MeOH. The resulting MeOH solution was concentrated and subsequently EtOAc (and a little absolute MeOH) was added, the latter solution being dried on $MgSO_4$. After removal of the drying agent and the solvent in vacuo, 6.1 g (96%) of the desired intermediate was isolated.

Step 2 (scheme C): 6.1 g (14 mmol) of the latter intermediate were dissolved in a mixture of 30 ml EtOAc and 70 ml of MeOH after which a catalytic amount of 10% Pd-C was added. Subsequently the mixture was hydrogenated at atmospheric pressure. After 16 hrs an extra amount of 10% Pd-C was added. Another 16 hrs later, the reaction mixture was filtered and concentrated in vacuo, leaving a residue which was subjected to flash column chromatography ($SiO_2$, eluent: $CH_2Cl_2$/MeOH/$NH_4$OH=92/7.5/0.5), yielding 2.05 g (50%) of the primary amine.

Step 3 (scheme C): 2.05 g (7.1 mmol) of the latter primary amine were suspended in 9 ml of 1,2-dimethoxy-ethane, after which 1.32 g (35 mmol, 5 eq.) of $NaBH_4$ were added. Then the mixture was brought to 0° C., after which a solution of 2.1 g (35 mmol) acetic acid in 7 ml 1,2-dimethoxy-ethane was carefully added to the mixture. When the addition was completed, the reaction mixture was brought to 85° C. After a period of 1 hour the reaction was allowed to reach room temperature, the reaction mixture was acidified to pH 2 (aqueous 2 M HCl) and heated again until the temperature reached 60° C., which situation was continued for 0.5 hrs. After this period, the reaction mixture was allowed to reach room temperature again and its pH was adjusted to 7–8 by adding aqueous 2 M NaCl. Extraction was performed with EtOAc, the organic fraction was washed with saturated NaCl/water and dried on $Na_2SO_4$. After removal of the drying agent and the solvent in vacuo, 0.73 g (37%) of a yellow oil containing the reduced amine intermediate was obtained. This was used without further purification for step 4.

Step 4 (scheme C): 0.73 g (2.6 mmol) of the reduced amine intermediate and 0.53 g (5.3 mmol) of $Et_3N$ were dissolved in 35 ml $CH_3CN$. While stirring, a solution of 0.37 g (2.36 mmol) para-fluorobenzoyichloride in 7 ml of $CH_3CN$ was added slowly and dropwise. After 16 hrs the reaction mixture was concentrated in vacuo, leaving a residue which was subjected to flash column chromatography ($SiO_2$, eluent: $CH_2Cl_2$/MeOH=97/3), yielding an oil (free base) which was treated with 2.0 equivalents, of 0.5 M HCl/MeOH to give 0.3 g (24%) of hygroscopic C10.2HCl-salt. $[\alpha]_D^{25}$ –59° (MeOH, 12.0 mg/ml). $^1$H-NMR(CDCl$_3$/DMSO=¼) δ: 1.28(d, 3H, J=6 Hz), 3.0–3.7(cluster, 12H), 3.7–4.2(broad, 2H), 4.25(t, 2H, J=3 Hz), 4.57(m, 1H), 6.44–6.60(cluster, 2H), 6.72(t, 1H, J≈8 Hz), 7.25(m, 2H), 8.08(m, 2H), 8.8(d, 1 H, J≈8 Hz), 10.3(s broad, 1H).

Remark

The two diastereomeric compounds C8 and C9 were prepared by reacting the racemic piperazine XII-H with optically pure (R)-N-(benzyloxycarbonyl)-alanine following the synthetic pathway depicted in scheme C. After step 4 (scheme C) a diastereomeric mixture was obtained which was separated into its pure components by HPLC.

TABLE C

| compound | piperazine | Q | salt | melting point ° C. |
|---|---|---|---|---|
| C1 | XI | 19 | 2HCl | 182–4 |
| C2 | XI | 16 | 2HCl | 238–43 |
| C3 | XI | 17 | 2HCl | 240–3 |
| C4 | XI | 18 | 2HCl | 216–9 |
| C5 | XI | 20 | 2HCl | >180 d |
| C6 | XI | 22 | 2HCl | 175 |
| C7 | XI | 21 | 2HCl | >168 d |
| C8 | XIII or XIV | 17 | 0.5FUM | amorf |
| C9 | XIV or XIII | 17 | 0.67FUM | amorf |
| C10 | VIII | 17 | 2HCl | $[\alpha]_D^{25}$–59° |
| C11 | XI | 32 | 2HCl | 178–83 d |
| C12 | XI | 23 | 2HCl | 193–9 d |
| C13 | XI | 24 | 2HCl | 175–80 |
| C14 | XI | 28 | 2HCl | 173–8 d |
| C15 | XI | 31 | 2HCl | >165 d |
| C16 | XI | 25 | HCl | 115–20 d |
| C17 | XI | 26 | HCl | 220–5 d |
| C18 | XI | 27 | HCl | 130–5 d |
| C19 | XI | 29 | 2HCl | 220–2 |
| C20 | XI | 30 | 2HCl | 225 |

Example 6

Preparation of D1 (See Scheme D)

0.94 g (4.3 mmol) of piperazine I-H together with 0.77 g (4.3 mmol) of (R)-2-para fluorphenyl-4-methyl-4,5-dihydro-oxazole (vide infra) and 0.16 g (0.84 mmol) of para-toluenesulfonic acid were dissolved in 4 ml of N-methyl-pyrrolidone. The mixture was stirred under a nitrogen atmosphere at 135° C. After 12 hrs the reaction mixture was allowed to reach room temperature after which 40 ml of EtOAc, 20 ml of water and 4 ml of aqeous 2 M NaOH were added. The latter mixture was shaken vigorously, and after standing, the organic fraction was separated and washed with water and dried on $Na_2SO_4$. The drying agent was removed by filtration, to the filtrate $SiO_2$ was added, after which the solvent was removed. The resulting dry $SiO_2$ powder with the organic fraction absorbed on it, was placed on top of a dry $SiO_2$ column (flexible), after which elution was performed with $CH_2Cl_2$/MeOH=87/13. The product-containing part of the column was cut out and the product was washed from the $SiO_2$ with MeOH. The resulting MeOH solution was concentrated and subsequently $CH_2Cl_2$/MeOH=80/20 was added, the latter solution being dried on $Na_2SO_4$. After removal of the drying agent and the solvent in vacuo, a solid was isolated which was suspended in EtOAc/EtOH=5/1 and stirred for 0.5 hrs at reflux temperature. After the suspension had reached room temperature, filtration took place yielding a residue: 0.29 g (16%) of pure D1. m.p.: 240–2° C. $^1$H-NMR(CDCl$_3$/DMSO=¼) δ: 1.19(d, 3H, J=6 Hz), 2.32–2.70(cluster, 6H), 3.12–3.22(m, 4H), 4.25(m, 1H), 6.56(m, 1H), 6.60(m, 1H), 6.98(t, 1H, J=8 Hz), 7.23(m, 2H), 7.92(m, 2H), 8.15(d, 1H, J=8 Hz), 11.5(broad, 1H).

Preparation of (R)-2-para fluorophenyl-4-methyl-4,5-dihydro-oxazole 25 g (0.21 mol) of para-fluorobenzonitrile together with 16.5 g (0.22 mol) of (R)-2-amino-1-propanol and 4.56 g (0.033 mol) of $K_2CO_3$ were mixed together in a solution of 70 ml of ethyleneglycol and 40 ml of glycerol. This mixture was heated at 105° C. for 24 hrs, under a nitrogen atmosphere, after which the reaction mixture was allowed to reach room temperature. Subsequently 150 ml of n-hexane and 300 ml of water were added, the resulting mixture was agitated after which the organic fraction was separated and dried on $Na_2SO_4$. After removal of the drying agent and the solvent in vacuo, 15 g (40%) of the crude oxazol was isolated as a yellow oil. This was used without further purification in the syntheses of the D-compounds.

Remark

D3 was made in the following way:

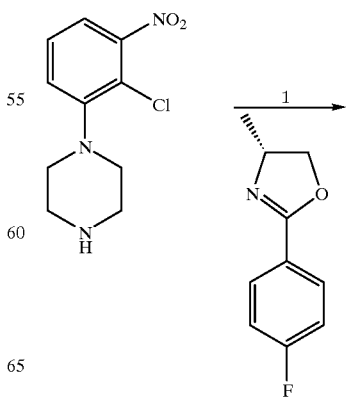

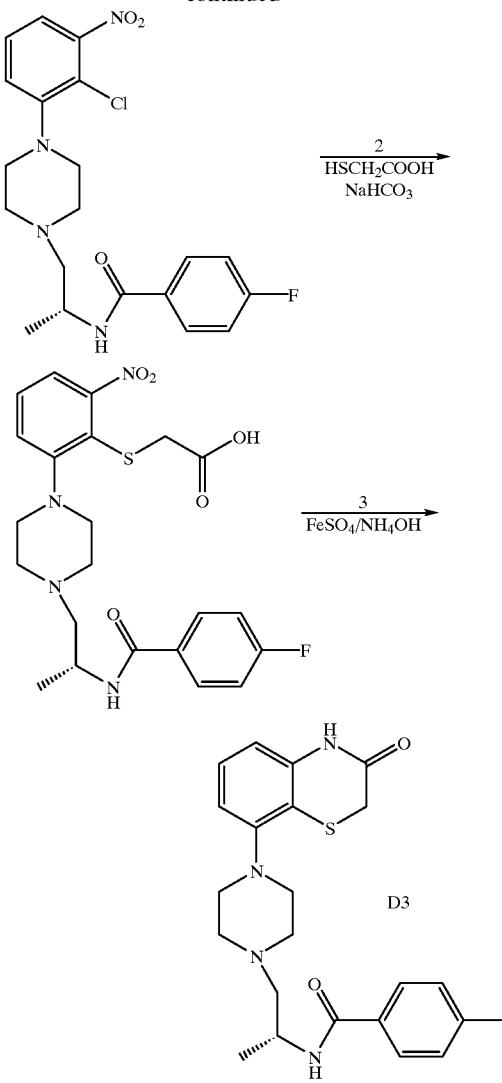

Step 1 was carried out analogously to the preparation of D1 (see example 6), steps 2 and 3 were carried out analogously to the syntheses described by Cechetti, *Eur J. Med. Chem.*, 24, (1989), 479, the disclosure of which is incorporated herein by reference.

TABLE D

| compound | piperazine | Q | salt | melting point ° C. |
|---|---|---|---|---|
| D1 | I | 17 | — | 240–2 d |
| D2 | VII | 17 | — | 250–2 |
| D3 | X | 17 | — | 237–8 |
| D4 | III | 17 | — | 187–9 |
| D5 | IV | 17 | 2.HCl | 150 d |
| D6 | V | 17 | HCl | 225–7 d |
| D7 | XVII | 17 | HCl | 148–52 d |
| D8 | XVIII | 17 | HCl | $[\alpha]_D^{25}$ –46° |

INTERMEDIATES used in route A
Step 1 (scheme i)
3.94 g (21.9 mmol) of 7-nitro-2-benzoxazolidinone (for preparation of the latter compound, see EP 0189612 and references cited therein), were dissolved in 40 ml of DMSO after which 1.72 g of 85% powdered KOH (26.2 mmol) were added. While stirring and cooling (water) 3.72 g (26.2 mmol) of MeI dissolved in 6 ml of DMSO, were added dropwise over a period of 10 minutes. Stirring was continued at room temperature for 16 hrs, during the latter period an extra amount of MeI (0.5 g) was added. After the reaction was completed, the reaction mixture was diluted with water after which extraction took place with $CH_2Cl_2$. The combined organic fractions were washed with water and brine respectively, after which the organic fraction was dried on $MgSO_4$. After removal of the drying agent and evaporation of the solvent in vacuo, 4.1 g of a solid residue was left. Flash column chromatography ($SiO_2$, eluent: $CH_2Cl_2$) of the latter yielded 3.6 g (85%) of pure 3-methyl-7-nitro-2-benzoxazolidinone.

Steps 2 and 3 were carried out as described in EP 0189612
Step 1 (scheme ii)
10.6 g (42 mmol) of (2,6-dinitro-phenyl)-acetic acid methyl ester was dissolved in a mixture of 200 ml of EtOAc and 50 ml of MeOH. A catalytic amount of 10% Pd-C was added and the solution was shaken under atmospheric $H_2$ pressure at room temperature. After the calculated amount of $H_2$ was taken up by the reaction mixture, the catalyst was removed by filtration and the filtrate concentrated in vacuo. It was attempted to crystallize the wanted intermediate from warm EtOAc, however, only darkening of the solution occurred. Removal of the solvent and subsequent flash chromatography of the residue ($SiO_2$, eluent: $CH_2Cl_2$/MeOH=97/3) yielded 4.6 g (74%) of the wanted aniline as a brown solid.

Step 2 (scheme ii)
1.4 g (9.4 mmol) of the aniline and 4.1 g (9.9 mmol) of $TosN(CH_2CH_2OMs)_2$ were dissolved in 40 ml of chlorobenzene. While stirring, 4.35 ml (25 mmol) of diisopropylethylamine were added after which the temperature was raised to 140° C. for 8 hrs. After the reaction mixture had reached room temperature, it was concentrated in vacuo and subsequently the residue was subjected to flash chromatography ($SiO_2$, eluent: $CH_2Cl_2$/MeOH 97/3) which yielded 0.9 g (26%) of a greenish solid containing the tosylated piperazine.

Step 3 (scheme ii)
0.9 g (2.4 mmol) was dissolved in 2 ml of concentrated HCl and heated at reflux temperature for 16 hrs after which the reaction mixture was allowed to reach room temperature. The mixture was filtered (Hyflo) and the filtrate was exhaustively concentrated in vacuo after which the residue was washed with diethylether. Yield: 0.95 g (100%) of III-H.TosOH.

Step 1 (scheme iv)
42 g (0.22 mol) of the nitroquinoline were suspended in 1000 ml of 96% EtOH. To the latter solution 19.5 g of 10% Pt-C/$H_2O$ was added. While stirring, the mixture was hydrogenated under a pressure that eventually reached 4 atmospheres; in the beginning of the reaction the consumption of hydrogen was so fast that the pressure could not reach 4 atmospheres instantly. For 2 days the reaction was continued, during the nights the mixture was put under a nitrogen atmosphere. After this period, the catalyst was removed by filtration and the filtrate concentrated in vacuo leaving 35.5 g of crude product which was subjected to column chromatography ($SiO_2$, eluent: $CH_2Cl_2$/MeOH=99/1), yielding 25 g (70%) of the desired product.

Step 2 (scheme iv)
This step is similar to step 2 described in scheme ii.
Step 3 (scheme iv)
0.7 g (1.7 mmol of the N-tosyl homopiperazine was dissolved in 20 ml of concentrated HCl after which the mixture was refluxed for 16 hrs. After the reaction mixture had reached room temperature, it was poured into an aqeous $K_2CO_3$ solution. The basic mixture was extracted with EtOAc after which the organic fraction was dried on $MgSO_4$. After removal of the drying agent and evaporation of the solvent in vacuo, the residue was subjected to flash column chromatography ($SiO_2$, eluent: $CH_2Cl_2$/MeOH/$NH_4OH(25\%,aq)=92/7.5/0.5$), which yielded 0.4 g (96%) of IX-H as a brownish oil.

Step 1 (scheme vi)

1.2 g (3.6 mmol) of the N-benzytpiperazine derivative (which can be prepared analogously to the procedure described for the synthesis of 1-[5-(1,4)-benzodioxanyl)]-trans-3,5-dimethyl-piperazine, see EP 0189612) was dissolved in 50 ml of EtOAc/MeOH=1/1, after which a catalytic amount of 10% Pd-C was added. The solution was agitated under atmospheric $H_2$-pressure for 60 hrs. After the latter period the catalyst was removed by filtration, the filtrate concentrated in vacuo, after which the residue was subjected to flash column chromatography ($SiO_2$, eluent: $CH_2Cl_2$/MeOH/$NH_4OH(25\%,aq)=92/7.5/0.5$) yielding 0.7 g (80%) of XV-H as a yellow oil which solidified on standing.

Step 1 (scheme vii)

0.5 g (2.1 mmol) of the oxime was added to 5 g of polyphosphoric acid which was heated at 110° C. After 0.5 hrs, the warm (T<80° C.) reaction mixture was poured into saturated aqeous $NaHCO_3$ solution. After a while extraction was performed with EtOAc after which the organic fraction was dried on $Na_2SO_4$. After removal of the drying agent and evaporation of the solvent in vacuo, 0.42 g (84%) of solid azepinone was left.

Step 2 (scheme vii)

100 ml of toluene were flushed with $N_2$. 0.96 g (4 mmol) of the azepinone, 2.75 g (32 mmol, 8 eq.) of piperazine, 5.2 g (36 mmol, 9 eq.) of NaOtBu, 0.04 g (0.04 mmol, 0.01 eq.) of $Pd_2(dba)_3$ and 0.082 g (0.12 mmol, 0.03 eq.) of (R)-(+)-BINAP were added to the toluene. The mixture was brought to a temperature of 80° C. for 16 hrs. After cooling the solution was concentrated in vacuo, after which the residue was subjected to flash column chromatography ($SiO_2$, eluent: $CH_2Cl_2$/MeOH/$NH_4OH(25\%,aq)=92/7.5/0.5$), yielding 0.95 g of reddish material. The latter was treated with aqueous 2 M NaOH after which extraction took place with $CH_2Cl_2$. The organic fraction was washed with water and dried on $Na_2SO_4$ and a little charcoal was added. After removal of the drying agent and charcoal by filtration and evaporation of the solvent in vacuo, 0.56 g (57%) of light yellow XVII-H was isolated.

Intermediate used in Example 3

For the synthesis of A23, O-mesyl-N-benzyloxycarbonyl-(R)-alaninol was used, the synthesis of this intermediate was performed as follows:

2.0 g (8.4 mmol) of N-benzyloxycarbonyl-(R)-alanine methyl ester were dissolved in 20 ml of MeOH, after which 0.96 g (25 mmol) of $NaBH_4$ was added carefully (foam). Stirring was continued for 1 hr at room temperature after which the reaction mixture was acidified (2 M HCl) to about pH 2. EtOAc was added and after agitation the organic fraction was separated and dried on $Na_2SO_4$. After removal of the drying agent and the solvent in vacuo, leaving 1.8 g of a colorless oil, containing the N-benzyloxycarbonyl-(R)-alaninol. The latter compound was transformed into its corresponding mesylate by the standard treatment with tri-ethylamine in $CH_2Cl_2$ at −5° C. after which mesylchloride added. After work-up 74% of the corresponding mesylate could be isolated as a white solid.

Intermediates Q-Cl and Q-Br

Q3-Cl was prepared from commercially available 3-bromo-2-methyl-1-chloro-propane and para-fluorphenol 2.45 g (106.5 mmol) of Na was reacted with 75 ml of absolute EtOH after which, while stirring, 10.0 g (89 mmol) of para-fluorphenol was added. The resulting solution was added dropwise to a warm solution of 45.8 g (267 mmol, 3 eq.) of 3-bromo-2-methyl-1-chloro-propane in about 20 ml of absolute EtOH. Stirring at reflux temperature was continued for 40 hrs. After cooling, the precipitate was removed by filtration, subsequently the filtrate was concentrated in vacuo and the residue treated with 2 M NaOH. The resulting solution was extracted with $Et_2O$. The combined organic fractions were washed with water and dried on $Na_2SO_4$. After removal of the drying agent and the solvent in vacuo, 26 g of a yellow oil was left. Dry chromatography ($SiO_2$, eluent: petroleum benzin) yielded 9.9 g (54%) of Q3-Cl. This amount was contaminated (ca. 30%) with the HCl eliminated side product of Q3-Cl. However, this batch was well suited for reaction with the described piperazines (see scheme Al).

Q9-Br was prepared in a Friedel-Craft reaction from racemic 4-bromo-2-methyl-butyryl bromide (for preparation see E. E. Ziegler et.al., J. Am. Chem. Soc., 112(1990)2755, the disclosure of which is incorporated herein by reference) and fluorobenzene While stirring at room temperature and under a nitrogen atmosphere, 6.8 g (51 mmol) of $AlCl_3$ were suspended in 70 ml of 1,2-dichloro-ethane. Then 11.5 g (47 mmol) of racemic 4-bromo-2-methyl-butyryl bromide were added dropwise to the mixture. After 10 minutes the mixture was brought to 15° C. after which 14 ml (149 mmol, 3.2 eq.) of fluorobenzene was added dropwise. No change in temperature occurred. Stirring was continued for 18 hrs at room temperature, after which the reaction mixture was worked up carefully with water (temperature was kept below 40° C.). An extra amount of 1,2-dichloro-ethane was added. The biphasic system was separated and the organic layer was washed with water. Subsequently the organic layer was dried on $Na_2SO_4$. After removal of the drying agent and the solvent in vacuo, 10.7 g (88%) of Q9-Br resulted as a yellow oil. This almost pure oil was used for the reactions with the described piperazines (see scheme A1).

Q10-Br was prepared in a two-step synthesis. Step 1: commercially available (S)-2-oxo4-methyl-tetrahydrofuran was reacted with $PBr_3$ according to the procedure described by E. E. Ziegler et.al., *J. Am. Chem. Soc.*, 112(1990)2755, the disclosure of which is incorporated herein by reference, giving (S)-4-bromo-3-methyl-butyryl bromide in 39% yield. Step 2: the latter compound was reacted with fluorobenzene in a Friedel-Craft reaction according to the procedure given for Q9-Br yielding 78% of the wanted product (vide supra). The obtained Q10-Br appeared not to be a good alkylating agent, therefore the diethylketal was prepared by treating Q10-Br with tri-ethoxymethane: 1.0 g (3.9 mmol) of Q10-Br was dissolved together with 1.14 g (7.72 mmol) of ethylorthoformiate $(CH_3CH_2O)_3CH$ in 1.0 ml of absolute ethanol. After 5 minutes 1 small drip of 5 M $H_2SO_4$ was added. Stirring was continued for 16 hrs at room temperature after which the reaction mixture was concentrated in vacuo, leaving a dark residue of crude diethylketal of Q10-Br. The latter preparation was used without further purification for the synthesis of compound A20.

Q-OH

Q2-OH was prepared from $NaOCH_2CH_2OH$ and p-fluorobenzylbromide: 2.75 g (0.12 mol) of Na was reacted with an ample amount of absolute methanol. After the reaction had been completed, the excess MeOH was removed in vacuo. To the remaining white solid 24 ml (2.75 g, 0.4 mol) of ethyleneglycol was added after which the temperature was raised to 170° C. After 3 hrs the reaction mixture was allowed to reach 80° C., at which temperature the liberated MeOH was removed in vacuo. Then, still at 80–90° C., 23.7 g (0.125 mol) of p-fluorobenzylbromide was added dropwise to the reaction mixture, after the addition was completed stirring and heating at 130° C. were continued for three hours. After reaching room temperature, the reaction mixture was poured into water. The latter mixture was extracted with EtOAc, and the combined organic fractions were washed with water and dried on MgSO$_4$. After removal of the drying agent and the solvent in vacuo, 21.3 g of an oily residue was left. Chromatography (silicagel, eluent: Et$_2$O/petroleum benzin 1/1) yielded 16.6 g (78%) of pure product Q2-OH.

Q4-OH was prepared from 3-hydroxy-1-butanol in three steps according to the procedure described in EP89009149, the disclosure of which is incorporated herein by reference: the first step being the protection of the primary alcohol group with the tert. butylcarbonyl moiety. The second step being a Mitsunobu reaction between the latter compound and para-fluorphenol. The third step, the deprotection of the primary hydroxy group, gave the desired Q4-OH in 32% overall yield.

Q5-OH was prepared similarly to the procedure described in H. Haubenstock et.al., *J. Am. Chem. Soc.*, 84(1962)2372, the disclosure of which is incorporated herein by reference.

Q6-OH was prepared from commercially available (S)-3-bromo-2-methyl-1-propanol and para-fluorphenol:

7.56 g (49.4 mmol) of (S)-3-bromo-2-methyl-1-propanol and 11 g (98 mmol) of para-fluorphenol were dissolved in 150 ml of acetone after which 18 g (130 mmol) of powdered K$_2$CO$_3$ were added. The reaction mixture was brought to refluxing temperature for a period of 24 hrs. After the reaction mixture had reached room temperature, the solvent was removed in vacuo leaving a residue which was dissolved in ethyl acetate/water. The organic layer was washed subsequently with 2 N NaOH and water (2x), after which the solution was dried on MgSO$_4$. After subsequent removal of the drying agent and the solvent, the residue was subjected to flash chromatography (SiO$_2$, eluent: petroleum benzin/methyl-tert.-butyl ether 2/1), which eventually yielded 4.65 g (25.1 mmol, 51%) of a colorless oil containing Q6-OH.

Q7-OH was prepared from commercially available (R)-3-bromo-2-methyl-1-propanol and para-fluorphenol in the same way as Q6-OH (vide supra).

The above described Q-OH were converted into their corresponding mesylates and tosylates by standard procedures, e.g. MsCl/Et$_3$N and TosCl/pyridin respectively. See also Table A1 (vide supra).

Q11 and Q12 are introduced in the compounds as described in scheme A2 (vide supra).

Q13, Q14 and Q15 are introduced in the compounds as described in scheme B1 (vide supra).

Q16–32 are introduced in the compounds as described in scheme C1 (vide supra). Q17 can also be introduced as described in scheme D1.

It will be apparent to those skilled in the art that various modifications and variations can be made in the compounds and methods of the invention without departing from the spirit or scope of the invention. Thus, it is intended that the present invention cover the modifications and variations of this invention provided that they come within the scope of the appended claims and their equivalents.

What is claimed is:

1. A compound having formula (a)

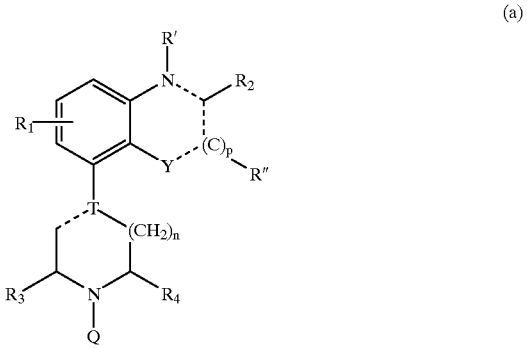

(a)

wherein

R$_1$ is hydrogen or fluoro,

R' is H or C$_{1-4}$-alkyl,

R$_2$ is H, C$_{1-4}$-alkyl, or an oxo group, or R' and R$_2$ together represent a single bond, R" is H or C$_{1-4}$-alkyl, and the dotted lines represent a single or double bond, p has the value 1, Y represents C, T represents N, R$_3$ and R$_4$ independently are hydrogen or C$_{1-4}$-alkyl, n has the value 1, Q is a group of the formula —CH$_2$—C(R$_5$R$_6$)—Z—R$_7$, wherein R$_5$ and R$_6$ represent H or C$_{1-7}$-alkyl, phenyl C$_{1-3}$-alkyl, Z represents —C(R$_8$R$_9$)—O—, —C(R$_8$R$_9$)—C(=O)—, —C(R$_8$R$_9$)—C(=NOR$_{10}$)—, —NH—C(=O)— or —O—CH$_2$—, wherein R$_8$, R$_9$ and R$_{10}$ represent H or C$_{1-4}$-alkyl; and R$_7$ is a 5- or 6-membered cyclic group, 5- or 6-membered aromatic group or 5- or 6-membered hetero-aromatic group, or the 1- or 2-adamantyl group, which R$_7$ group can be substituted with O—C$_{1-4}$-alkyl, CN, halogen or C—$_{1-4}$-alkyl, with the proviso that R$_7$ cannot be 1-alkylcycloalkyl, and that compounds of formula (a) wherein Z is the group —NH—C(=O)—, R$_5$=R$_6$=H, T is nitrogen, and the bicyclic group is 1,4-benzoxazin-8-yl, quinoxalin-5-yl, quinolin-5-yl, indol-4-yl, benzoxazol-7-yl, benzimidazol-4-yl, or benzothiazol-7-yl are not included, or a pharmaceutically acceptable salt thereof.

2. The compound according to claim 1, wherein T represents nitrogen, and R' is hydrogen.

3. The compound according to claim 1, wherein Y is carbon, T is nitrogen, p=1, n=1, R$_1$, R', R$_2$, R", R$_3$ and R$_4$ are hydrogen, the dotted lines are single bonds, and Q is a group of the formula —CH$_2$—C(R$_5$R$_6$)—Z—R$_7$ wherein R$_5$ and R$_6$ represent H, C$_{1-4}$-alkyl or benzyl, Z is —C(R$_8$R$_9$)—C(=O)—, —C(R$_8$R$_9$)—O— or —NH—C(=O)—, wherein R$_8$ and R$_9$ represent hydrogen or methyl, and R$_7$ is phenyl optionally substituted with halogen, CN, CH$_3$ or OCH$_3$.

4. The compound according to claim 3, wherein Z is —NH—C(=O)— or —CH$_2$-O—, R$_5$=H and R$_6$ is alkyl or alkylphenyl, and the chiral carbon atom carrying R$_5$ and R$_6$ is in the R-configuration.

5. A pharmaceutical composition, said composition comprising a pharmaceutically effective amount of at least one compound of formula (a) according to claim 1, and a pharmaceutically acceptable carrier.

6. A method of preparing a composition for treating a CNS-disorder, said method comprising including in said composition a pharmaceutically effective amount of at least one compound of formula (a) according to claim 1 and a pharmaceutically acceptable carrier.

7. A method of treating a CNS-disorder, said method comprising administering to a host in need of said treatment an effective amount of a compound of formula (a) according to claim 1.

8. A method of treating schizophrenia, said method comprising administering to a host in need of said treatment an effective amount of a compound of formula (a) according to claim 1.

* * * * *

UNITED STATES PATENT AND TRADEMARK OFFICE
CERTIFICATE OF CORRECTION

PATENT NO. : 6,214,829 B1
DATED : April 10, 2001
INVENTOR(S) : Feenstra et al.

Page 1 of 1

It is certified that error appears in the above-identified patent and that said Letters Patent is hereby corrected as shown below:

<u>Column 28, claim 1,</u>
Line 25, "dofted lines" should read -- dotted lines --.

<u>Title page, Item [57],</u>
Line 3 of Abstract, "disdosed" should read -- disclosed --;
Line 5, (first line below formula (a), before "and salts thereof" insert -- wherein the radicals are as defined within, --.

Signed and Sealed this

Thirtieth Day of October, 2001

Attest:

NICHOLAS P. GODICI
Attesting Officer      Acting Director of the United States Patent and Trademark Office